US009526828B2

(12) United States Patent
Koehler

(10) Patent No.: US 9,526,828 B2
(45) Date of Patent: Dec. 27, 2016

(54) FLOW-CONTROLLING CATHETER HUB

(75) Inventor: Cleve Koehler, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 441 days.

(21) Appl. No.: 13/354,421

(22) Filed: Jan. 20, 2012

(65) Prior Publication Data

US 2012/0259292 A1  Oct. 11, 2012

Related U.S. Application Data

(60) Provisional application No. 61/472,724, filed on Apr. 7, 2011.

(51) Int. Cl.
*A61M 5/168* (2006.01)
*A61M 25/00* (2006.01)
*A61M 39/20* (2006.01)

(52) U.S. Cl.
CPC ..... *A61M 5/16813* (2013.01); *A61M 25/0097* (2013.01); *A61M 39/20* (2013.01)

(58) Field of Classification Search
CPC .............. A61M 39/22; A61M 2039/22; A61M 2039/2473; A61M 2039/267; A61M 2039/268; A61M 25/0075; A61M 25/0028; A61M 25/0029; A61M 25/003; A61M 2001/0035; A61M 39/26; A61M 5/168; A61M 5/16804; A61M 5/16877; A61M 5/16813; A61M 5/16881; A61M 25/0097; A61M 39/20; F16K 1/38
USPC ......... 251/209, 158, 215, 264; 604/533–537, 604/30, 32, 167.03, 167.05, 248
See application file for complete search history.

(56) References Cited

U.S. PATENT DOCUMENTS

| 1,451,025 | A | * | 4/1923 | Kraft ............................. 251/347 |
| 3,868,973 | A | * | 3/1975 | Bierman et al. ................ 138/43 |
| 4,269,387 | A | * | 5/1981 | Reynolds et al. ............ 251/122 |
| 4,615,485 | A | * | 10/1986 | Larson et al. ................ 239/124 |
| 4,807,847 | A | * | 2/1989 | Martz ........................... 251/144 |

(Continued)

OTHER PUBLICATIONS

American Modeler Magazine 1961, L.M. Cox Manufacturing Co., Inc. Advertisement for "Thimble-Drome "Takes" the Nationals in 1/2A". [retrieved Apr. 1, 2014]. Retrieved from the Internet: <URL: http:// http://www.airplanesandrockets.com/magazines/Thimble-Drome-Cox-049-1961-AM-Annual.htm.

(Continued)

*Primary Examiner* — Manuel Mendez
*Assistant Examiner* — Nicholas Meghri
(74) *Attorney, Agent, or Firm* — Woodard, Emhardt, Moriarty, McNett & Henry LLP

(57) ABSTRACT

Among other things, a flow-controlling catheter hub configured to connect with and adjust fluid flow to a catheter is shown. The hub includes a main body, a valve, and a luer fitting adapter. The main body, valve, and luer fitting adapter each have an interior passageway to receive and conduct fluid flow when the parts are assembled together. The valve is configured to engage the interior passageway of the main body to block fluid flow when the valve is in a closed position. When the valve is in an open position the valve is moved away from the interior passageway of the main body and fluid flows through the interior passageway of the main body. The luer fitting adapter freely rotates in the valve while the valve is adjusted relative to the main body. Adjustment of fluid flow to the catheter is possible without disturbing connections between parts.

20 Claims, 10 Drawing Sheets

(56) References Cited

U.S. PATENT DOCUMENTS

| | | | |
|---|---|---|---|
| 5,620,427 A | 4/1997 | Werschmidt et al. | |
| 5,702,374 A | 12/1997 | Johnson | |
| 5,984,373 A | 11/1999 | Fitoussi et al. | |
| 6,332,633 B1* | 12/2001 | Fitoussi et al. | 285/332 |
| 6,673,059 B2 | 1/2004 | Guala | |
| 7,601,147 B2 | 10/2009 | Waller et al. | |
| 2009/0102192 A1* | 4/2009 | Ziman | 285/401 |
| 2010/0076384 A1* | 3/2010 | Trask | A61M 39/06 604/248 |

OTHER PUBLICATIONS

Cox B10 Engine. [retrieved Apr. 1, 2014]. Retrieved from the Internet: <URL: http://www.coxengineforum.com/13889-curious-about-cox-engines.

Cox Engine Operation Guide 2013. [retrieved Apr. 1, 2014]. Retrieved from the Internet: <URL: http:// http://coxengines.ca/files/EOG.pdf>.

* cited by examiner

FLOW-CONTROLLING CATHETER HUB

REFERENCE TO RELATED APPLICATION

This application claims the benefit of U.S. Provisional Application No. 61/472,724, filed Apr. 7, 2011, which is hereby incorporated by reference.

BACKGROUND

The present disclosure relates generally to a flow-controlling catheter hub and more particularly to a valve within the hub that is configured to adjust the range of fluid flow through a catheter from a closed position to a fully opened position and a luer fitting adapter that is configured to move independently of the valve.

Frequently during use of a single-lumen or multi-lumen catheter, such as an intravenous catheter or a hemodialysis catheter, it is required to stop or slow the flow of fluid through the catheter. Typically a plastic clamp is placed on the tubing between a manifold and a luer fitting or hub to control the flow of fluid through the catheter. These plastic clamps can have several disadvantages. Among these are that such plastic clamps are often packaged with a catheter, and the plastic clamps require additional packaging space and packaging materials. The clamps tend to be big and bulky, and when the plastic clamps are attached or clamped to the catheter tube, the bulkiness and size of the clamps can add to patient discomfort. When plastic clamps are attached to the catheter tube, they tend to mechanically deform the catheter tube which will place a bend or kink in the tube which disrupts the flow of fluid through the tube. Further, when the plastic clamps are attached to larger French size catheters, the plastic clamps have a tendency to break. Thus, there is a need for improvement in this field.

SUMMARY

This Summary is provided merely to introduce certain concepts and not to identify any key or essential features of the claimed subject matter.

In certain of its aspects, the present disclosure features a flow-controlling catheter hub that is configured to adjust fluid flow to a catheter. The hub includes a plug, a valve, a main body, and a luer fitting adapter. The plug has a cylindrical shaft portion and a cone portion. The valve has a luer end opposite a catheter end and defines an interior passageway between the luer end and the catheter end. When the hub is assembled, the luer end of the valve is oriented in the direction of the luer fitting adapter and the catheter end is oriented in the direction of the catheter. The catheter end of the valve is configured to connect with a proximal end of the main body, and the catheter end is also configured to receive the cylindrical shaft portion of the plug wherein the cone portion of the plug extends from the catheter end. The luer end of the valve is configured to receive a distal end of the luer fitting adapter. The main body has a distal end opposite a proximal end and defines an interior passageway between the distal end and the proximal end. When the hub is assembled, the proximal end of the main body is oriented towards the valve and the distal end of the main body is oriented towards the catheter. The proximal end of the main body is configured to receive the catheter end of the valve. The distal end of the main body is configured to receive a portion of the catheter, and the distal end is also configured to selectively receive the cone portion of the plug to adjust the amount of fluid flow through the distal end of the main body between a closed position and a fully opened position. The luer fitting adapter has a distal end opposite a proximal end and defines an interior passageway between the distal end and the proximal end. The distal end of the luer fitting adapter is configured to connect with the luer end of the valve such that the luer fitting adapter can be removed or adjusted relative to the valve without interfering with the connection between the valve and the main body. The proximal end of the luer fitting adapter is configured to receive a medication delivery device such as an intravenous therapy.

In some embodiments, both the catheter end of the valve and the proximal end of the main body include a plurality of threads to threadably engage each other to couple the valve with the main body. In one embodiment, the interior passageway of the main body includes a portion that is tapered from a first opening that is sized to receive the cone portion of the plug to a smaller second opening that is sized to receive a catheter port or other portion of the catheter. In another embodiment, the valve includes a ridge on an exterior surface, and the interior passageway of the main body includes a stop ledge near the proximal end to contact the ridge and retain the catheter end of the valve within the main body. In yet another embodiment, the distal end of the luer fitting adapter has a band portion with a substantially smooth exterior surface, and the interior passageway of the valve includes a first ledge and a second ledge to retain the band portion therebetween.

In other of its aspects, the present disclosure features a flow-controlling catheter hub that is configured to adjust fluid flow to a catheter and is detachable from the catheter. The hub includes a plug, a valve, a main body, a first luer fitting adapter, and a second luer fitting adapter. In such embodiments, the second luer fitting adapter is connected to the catheter, and the main body is detachable from the second luer fitting adapter. The valve, main body, and first luer fitting adapter are assembled and function similarly to the above-noted aspects. Beneficially, a medical practitioner can gain access to the patient's vasculature by simply detaching the main body from the second luer fitting adapter and removing the valve, main body, and first luer fitting adapter, thereby exposing an interior passageway in the second luer fitting adapter. A new incision is not required for the patient since a medical device can be inserted through the interior passageway and into the vasculature of the patient. After the procedure, the main body is reattached to the second luer fitting adapter.

Further forms, objects, features, aspects, benefits, advantages, and embodiments of the present disclosure will become apparent from a detailed description and drawings provided herewith.

DESCRIPTION OF THE SELECTED EMBODIMENTS

Figure 1:
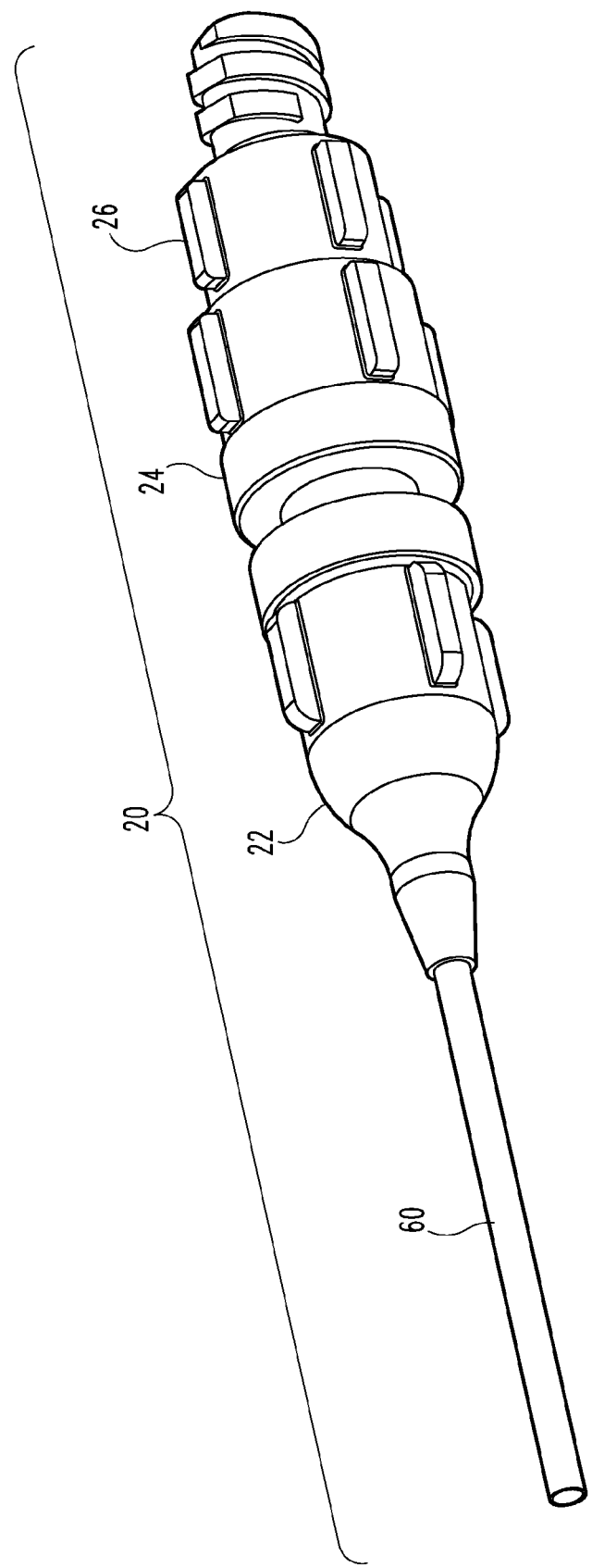
FIG. 1 is a perspective view of one embodiment of a flow-controlling catheter hub.
Figure 2:
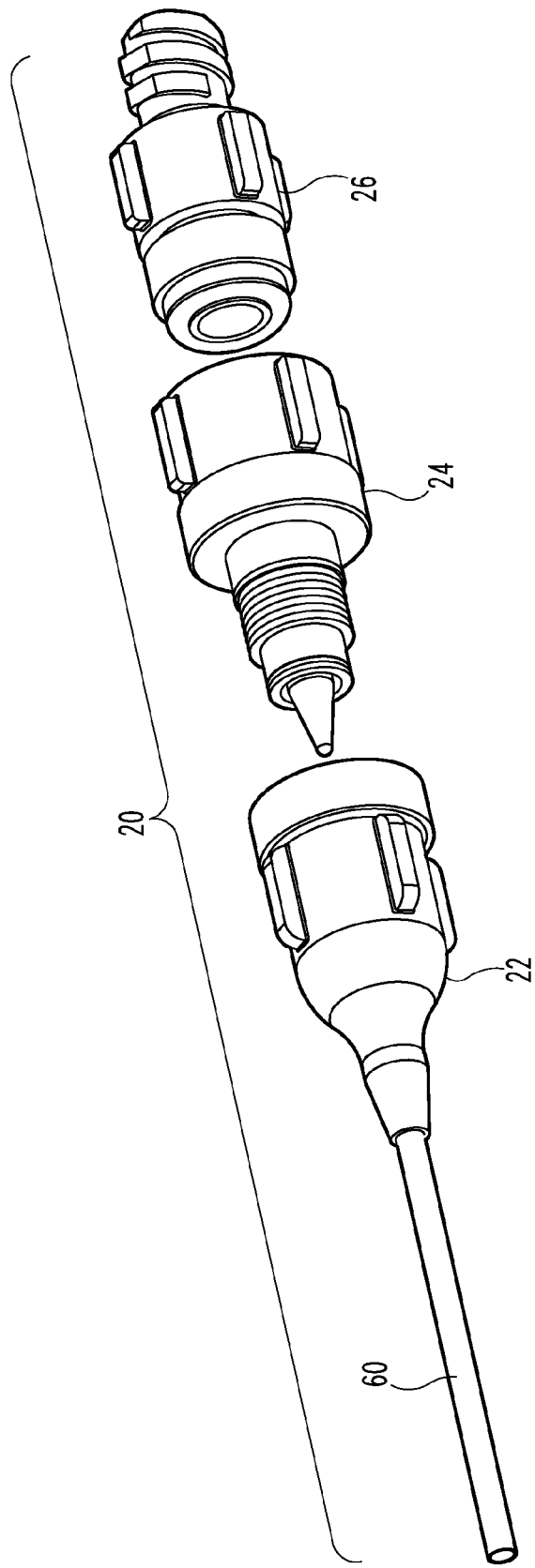
FIG. 2 is an exploded perspective view of the embodiment illustrated in FIG. 1.
Figure 3:
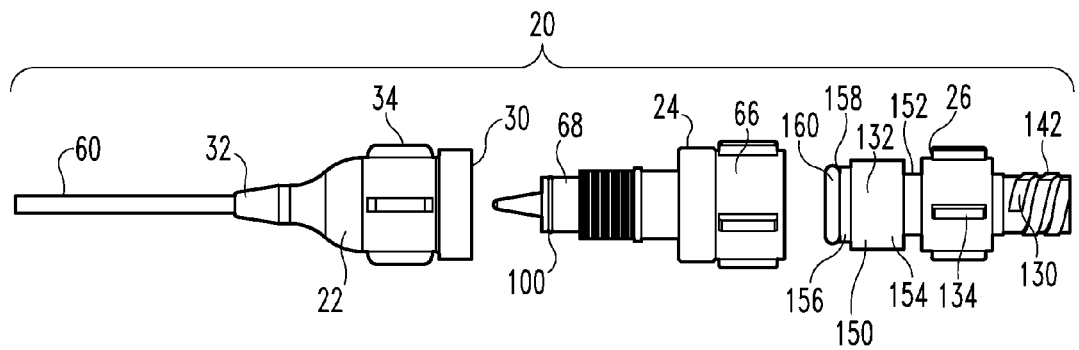
FIG. 3 is a side view of the embodiment illustrated in FIG. 2.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments and any further applications of the principles of the disclosure as described herein are contemplated as would normally occur to one skilled in the art to which the disclosure relates. Embodiments of structure are shown in detail, although it will be apparent to those skilled in the relevant art that some features that are not relevant to the present disclosure may not be shown for the sake of clarity.

The present disclosure features a flow-controlling catheter hub that is configured to adjust fluid flow to a catheter. A first embodiment of the flow-controlling catheter hub includes a plug, a valve, a main body, and a luer fitting adapter or female luer fitting. To form the hub, as will be discussed further, the catheter is connected with the main body and the plug is assembled with the valve, and the valve and main body are adjustably connected. In other embodiments, the valve and plug are one-piece, e.g. a needle valve or similar structure. The valve is assembled with the main body such that the plug is inserted into the main body. The luer fitting adapter or female luer fitting is assembled with the valve. In an assembled state, an interior passageway spans or extends through the luer fitting adapter, valve, and main body. The valve is configured to move between a closed position that stops fluid flow through the interior passageway of the main body and a fully opened position wherein a maximum amount of fluid flows through the interior passageway of the main body. The amount of fluid flow through the main body and catheter is adjusted by moving or rotating the valve relative to the main body. As the valve is rotated to the closed position, the plug engages the interior passageway of the main body to seal the interior passageway to stop fluid flow. When the valve is rotated to the open position, the plug no longer engages the interior passageway of the main body; therefore, fluid is able to flow through the interior passageway of the main body.

Beneficially, the medical practitioner can stop the amount of fluid flow through the main body, open the amount of fluid flow to a maximum amount, or adjust the fluid flow to an amount somewhere between closed and fully-opened. The luer fitting adapter and the valve move independently of each other and this independent movement is very beneficial for many reasons. Adjustment of the valve relative to the main body does not interfere or alter the connection between the luer fitting adapter and the valve. Also, adjustment of the luer fitting adapter relative to the valve does not interfere or alter the connection between the valve and the main body so that the amount of fluid flow is not affected or altered. Beneficially, when using the flow-controlling catheter hub, the catheter tube is not deformed since none of the parts of the hub are clamped onto the catheter tube. Moreover, the catheter can be any size, and the main body and interior passageway are sized accordingly. For example, if the catheter is a French size 9, then the interior passageway of the main body is about 3 millimeters.

Embodiments of a flow-controlling catheter hub may include a plug, a valve, and a luer fitting adapter or female luer fitting similar to the structures noted above, and a main body that is configured differently than the main body noted above. In particular embodiments a second female luer fitting is included that is configured to receive and retain a catheter. The main body has a male luer end that is configured to detachably connect to the second female luer fitting. Therefore, the male luer end of the main body can be detached from the second female luer fitting so that the hub can be partially or completely removed from the catheter. Beneficially, this allows a medical practitioner to insert a wire guide or other medical device through the second female luer fitting and into the catheter and the vasculature of the patient to perform other medical procedures. The plug, valve, main body, and luer fitting adapter are simply removed from the second female luer fitting thereby exposing the second female luer fitting and allowing access to the catheter. The position of the valve can be adjusted relative to the main body to thereby adjust the amount of fluid flow through the main body and the catheter. The luer fitting adapter can be rotated relative to the valve without interfering or altering the connection between the valve and the main body and hence the amount of fluid flow is not affected or altered.

In such embodiments, the catheter is not deformed since none of the parts of the flow-controlling catheter hub are clamped onto the catheter. Moreover, the catheter can be any size, and the second female luer fitting is sized accordingly. Further, since the main body connects with the second female luer fitting, a different size of the main body is not required when a different sized catheter is required.

Referring generally to FIGS. 1-4, an embodiment of a flow-controlling catheter hub 20 is illustrated. Hub 20 includes a main body 22, a valve 24, and a luer fitting adapter or female luer fitting 26 in this embodiment. As described in more detail below, valve 24 is configured to limit or adjust a range of fluid flow through the main body 22 from fully opened to closed. A completely closed position for valve 24 therefore blocks the fluid flow through the main body 22, whereas a partially-opened position for valve 24 permits a reduced amount of fluid flow through the main body 22 as compared to a fully-opened position for valve 24, which allows the maximum amount of fluid to flow through the main body 22. In this embodiment, the fluid flow is reduced by simply rotating the valve 24 clockwise, thereby partially blocking the fluid flow through main body 22 as described further below. Conversely, the fluid flow is increased by rotating valve 24 counterclockwise, as discussed further below, to allow more fluid to flow through the main body 22. In other embodiments, the fluid flow can be reduced or increased by moving valve 24 in a different manner. For example, valve 24 could move in a linear manner or slide in main body 22 without rotation. As described in more detail below, the luer fitting adapter 26 is able to move or rotate independently of the valve 24 and the main body 22. Valve 24 can thus be adjusted relative to main body 22 without loosening the connection between luer fitting adapter 26 and valve 24. Similarly, luer fitting adapter 26 can be adjusted relative to valve 24 without loosening the connection between valve 24 and main body 22.

Figure 7:
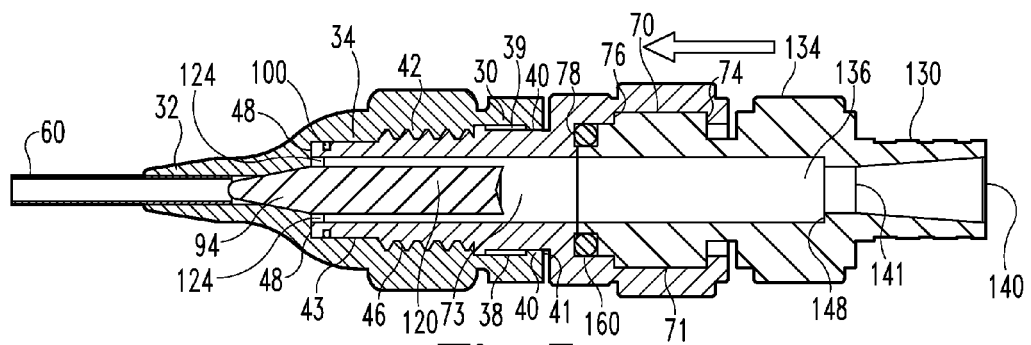
FIG. 7 is a cross-sectional view of the embodiment illustrated in FIG. 6.
Figure 8:
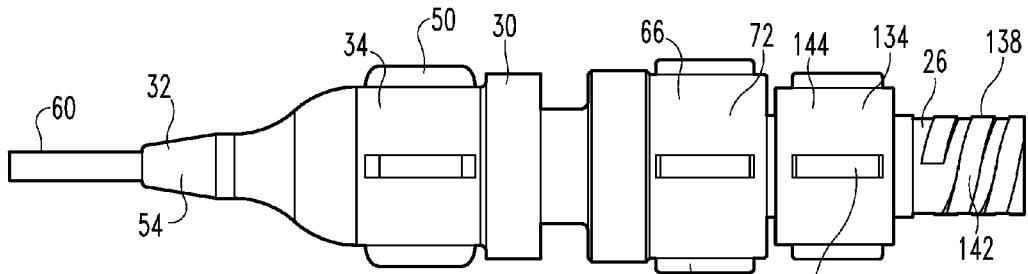
FIG. 8 is a side view of the embodiment illustrated in FIG. 1 with the valve in an open position.
Figure 9:
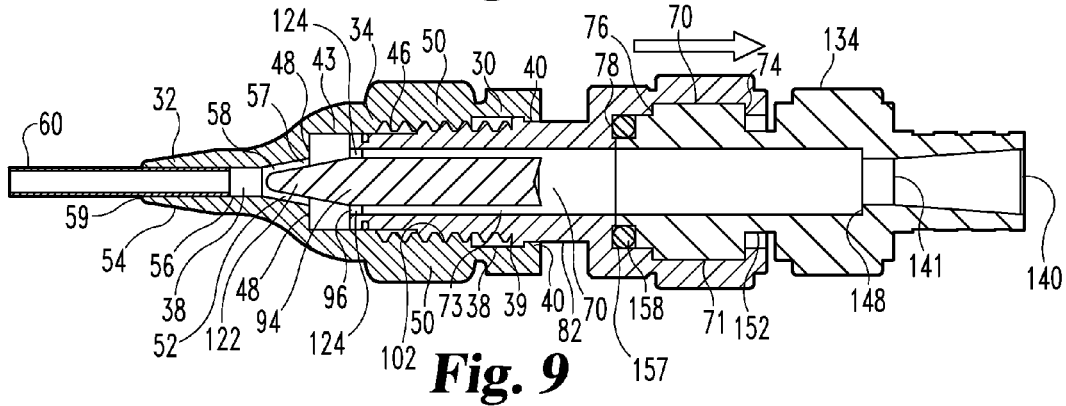
FIG. 9 is a cross-sectional view of the embodiment illustrated in FIG. 8.

The main body 22 has a proximal end 30 opposite a distal end 32 and a middle portion 34 therebetween. The main body 22 includes an interior passageway 38 that is sized to receive a distal end of the valve 24 and an end portion of a catheter tube 60 or a catheter port. The interior passageway 38 spans or extends from the proximal end 30 to the distal end 32. As described below, interior passageway 38 has several (e.g. five in this embodiment) different sections that interact with different portions of the valve 24 or catheter tube 60. Interior passageway 38 has a first section 39 with a stop ledge 40 positioned at an opening 41 as illustrated in FIGS. 7 and 9. As described in more detail below, the stop ledge 40 is sized to engage and retain a ridge 84 on valve 24 to maintain the assembly of the valve 24 with the main body 22. As such, the stop ledge 40 limits the rearward movement of the valve 24 beyond the proximal end 30 of the main body 22. Therefore, a user is not able to rotate or otherwise move valve 24 beyond the fully-open position when adjusting or determining desired flow, because the ridge 84 will engage the stop ledge 40. Additionally, the interaction of the ridge 84 on valve 24 and the stop ledge 40 provides a tactile indication for the user that the valve 24 is in the fully-open position (illustrated in FIG. 9).

The interior passageway 38 of middle portion 34 includes a second section 42 and a third section 43 as illustrated in FIGS. 7 and 9. Middle portion 34 also includes an exterior surface 44. The second section 42 includes threads 46 that are sized to threadingly mate with threads 102 on the valve 24 as described below. The length of the section of threads 46 corresponds in this embodiment to the distance the valve 24 can travel in main body 22. The third section 43 of interior passageway 38 is smooth and is about the same length and diameter as a catheter end 68 of the valve 24. The third section 43 of the interior passageway 38 also includes an end stop 48 that engages the catheter end 68 of the valve 24 in the closed condition to stop the forward movement of the valve 24 in the main body 22. In the illustrated embodiment, exterior surface 44 includes a plurality of ridges 50. The plurality of ridges 50 aid a medical practitioner in gripping or holding the main body 22. In other embodiments, the exterior surface 44 may be substantially smooth.

Distal end 32 of body 22 has a fourth section 52 and a fifth section 56 of the interior passageway 38 and an exterior surface 54 as illustrated in FIGS. 7 and 9. Fourth section 52 of the interior passageway 38 is tapered from a first opening 57 to a smaller, second opening 58. The first opening 57 is sized to receive a cone portion 122 of a plug 94 attached to valve 24 and the second opening 58 sized to receive and connect with a portion of catheter tubing 60 or a catheter port. The taper of the fourth section 52 is about the same slope as the cone portion 122 of the plug 94 attached to valve 24. In other embodiments, fourth section 52 may be configured differently. For example, fourth section 52 may not taper but instead is the same diameter as fifth section 56. In such an embodiment, cone portion 122 of plug 94 could also be shaped differently such as oval, round, ogival, parabolic, or any other shape that can form a seal with the fourth section 52. Typically, cone portion 122 of plug 94 does not have a rectangular shape since a non-tapered shape may not fully engage the interior passageway and may not adequately adjust the fluid flow. Fifth section 56 of the interior passageway 38 starts at second opening 58 and spans to a distal opening 59. Fifth section 56 of the interior passageway 38 is about the same or slightly smaller than the diameter of catheter tubing 60 to thereby retain catheter tubing 60 by a friction fit or an interference fit. In other embodiments, an adapter, a hub, a plastic cap, or a connector mechanism may be attached to fifth section 56 to receive and retain the catheter tubing 60 with the main body 22. In yet other embodiments, the catheter tubing 60 is glued to or inserted into the fifth section 56 of the interior passageway 38. In other embodiments, the end of the catheter tubing 60 may include barbs to engage the fifth section 56 of the interior passageway 38.

Figure 4:
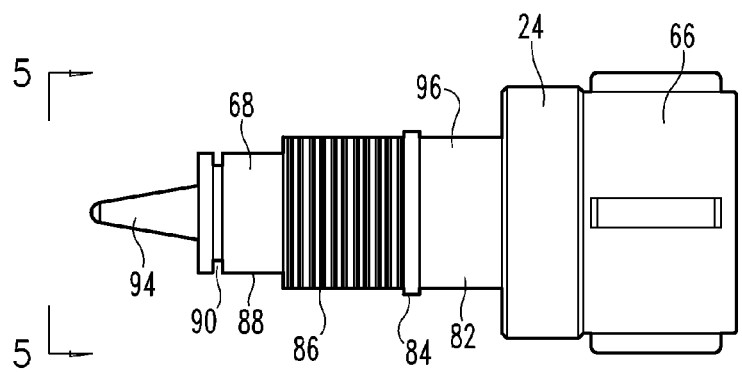
FIG. 4 is a partial view of the embodiment illustrated in FIG. 3.

Valve 24 has a luer end 66 opposite the catheter end 68 and an interior passageway 70 that spans the length of valve 24 as illustrated in FIGS. 4, 7, and 9. Luer end 66 is configured to receive and connect with the luer fitting adapter 26, whereas the catheter end 68 is configured to enter into and connect with the main body 22. Interior passageway 70 has a first section 71 and a second section 73. The first section 71 of the interior passageway 70 is substantially smooth such that the luer fitting adapter 26 can rotate (e.g. in free rotation) within valve 24 when luer fitting adapter 26 is assembled with valve 24. First section 71 of interior passageway 70 includes a first ledge 74, a second ledge 76, and a third ledge or end stop 78. The first ledge 74 and the second ledge 76 are sized and positioned to retain between them a band 154 on the luer fitting adapter 26 and maintain the connection between the luer fitting adapter 26 and the valve 24. The third ledge or end stop 78 is sized to engage an O-ring 157 placed on an O-ring receiving end 158 of the luer fitting adapter 26 to seal the connection between the luer fitting adapter 26 and valve 24. The third ledge or end stop 78 operates to the limit the forward distance the luer fitting adapter 26 is inserted into the valve 24. Luer end 66 also has an exterior surface 72. In the illustrated embodiment, exterior surface 72 includes a plurality of ridges 80. The plurality of ridges 80 aid a medical practitioner in gripping or holding the valve 24. In other forms, exterior surface 72 can be smooth.

Catheter end 68 includes a first portion 82, a ridge 84, a threaded portion 86, and a second portion 88 as illustrated in FIG. 4. The second portion 88 defines a groove 90 sized to receive an O-ring 100. In the illustrated embodiment, second section 73 of interior passageway 70 is sized to receive a plug 94. Second section 73 of interior passageway 70 is about the same diameter as an interior passageway 136 of luer fitting adapter 26 and spans the length of the catheter end 68. In the illustrated embodiment, first portion 82 includes a rounded or cylindrical exterior surface 96 that is substantially smooth. First portion 82 is sized to slide within or over the stop ledge 40 when the catheter end 68 is inserted in the main body 22. Ridge 84 is slightly larger in diameter than first portion 82, and ridge 84 is positioned adjacent first portion 82. Ridge 84 is sized to contact the interior of stop ledge 40 when the valve 24 is in the fully opened position. Threaded portion 86 includes threads 102 that are sized and arranged to engage threads 46 on middle portion 34 of main body 22. The length of threaded portion 86 corresponds to the length of second section 42 in the middle portion 34 of main body 22 in the illustrated embodiment. Second portion 88 is approximately the same diameter as the third section 43 of the interior passageway 38, and second portion 88 has a smooth exterior surface (cylindrical or rounded in this embodiment) to engage or seal to the third section 43 of the interior passageway 38 of middle portion 34 of main body 22. The O-ring 100 placed in groove 90 also aids in sealing the interior passageway 38.

Figure 5:
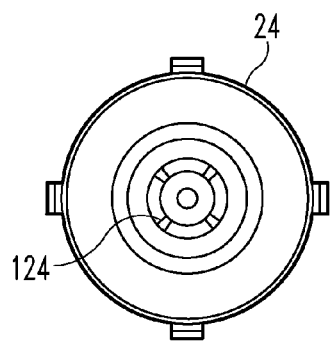
FIG. 5 is a front end view of the embodiment illustrated in FIG. 4.
Figure 6:
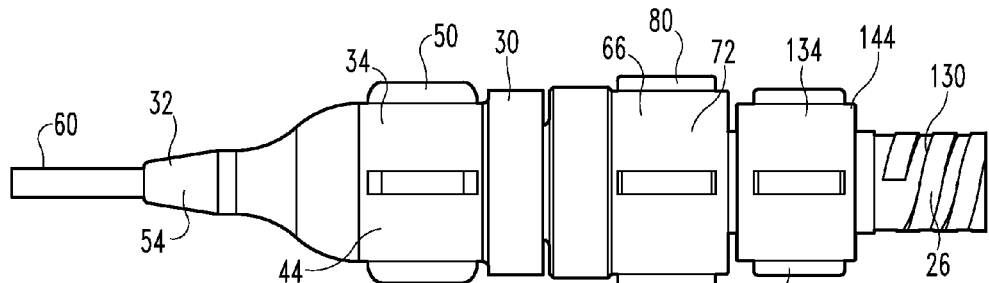
FIG. 6 is a side view of the embodiment illustrated in FIG. 1 with a valve in a closed position.

In the illustrated embodiment, plug 94 has a cylindrical shaft portion 120 and a cone portion 122. The cylindrical shaft portion 120 is sized to fit in the second section 73 of interior passageway 70 of valve 24. In particular, the cylindrical shaft portion 120 has a smaller diameter than the interior passageway 70 to allow fluid to pass through the interior passageway 70 and over the plug 94. The cylindrical shaft portion 120 includes a plurality of legs 124, as illustrated in FIG. 5, that are configured to attach to the interior passageway 70 when the plug 94 is assembled with the valve 24. In the illustrated embodiment, four legs 124 are shown, but other embodiments may include a different number of legs. In other embodiments, the plug 94 is attached to passageway 70 by a tongue-and-groove arrangement wherein the cylindrical shaft portion 120 may include one or more tongues and the interior passageway 70 includes a corresponding number of grooves to receive the tongues. The cone portion 122 has a conical shape that generally matches tapered section 52 and is sized to enter and move through second opening 58. When moved forward sufficiently, cone portion 122 meets tapered section 52 between, at or around one or both of openings 57 and 58, so that fluid does not flow past plug 94 when valve 24 is in the closed position. As mentioned previously, cone portion 122 of plug 94 could also be shaped differently such as oval, spherical, ogival, or any other shape that can form a seal with the fourth section 52 of the interior passageway 38 of the main body 22.

In other embodiments, hub 20 does not include a plug 94; instead the valve 24 is configured differently. In one form, the valve 24 includes a cap or rounded end projection that extends from the catheter end 68. The cap is configured to contact section 52 near or in first opening 57 to seal first opening 57 such that fluid does not flow past first opening 57 or section 52 when the valve 24 is in the closed position. As such, the cap is also configured to allow fluid flow through the cap when the valve 24 is in the open position or partially open position. In an alternate embodiment, the valve 24 and plug 94 are one piece or constructed monolithically, in the manner of a needle valve.

Turning now to luer fitting adapter 26, it includes a proximal portion 130 opposite a distal portion 132, a middle portion 134 between proximal portion 130 and distal portion 132, and an interior passageway 136 that spans from proximal portion 130 to the distal portion 132. The proximal portion 130 includes an exterior surface 138. In the illustrated embodiment, the exterior surface 138 includes threads 142 that are configured to mate and connect with threads from another medical device. In other embodiments, the exterior surface 138 may be smooth. The interior passageway 136 is tapered from a large distal opening 140 to a small interior opening 141 in the proximal portion 130. The portion of the interior passageway 136 from the large distal opening 140 to the small interior opening 141 is sized to receive a portion of a medical device that is inserted therein to deliver fluid through the interior passageway 136. For example, an intravenous bag could be attached to the large distal opening 140.

The middle portion 134 includes an exterior surface 144 that includes a plurality of ridges 146 that are similar to ridges 80. As such, ridges 146 aid a medical practitioner in gripping or holding the luer fitting adapter 26. In other forms, exterior surface 144 can be smooth. The interior passageway 136 widens at boss or ledge 148 from interior opening 141 in the proximal portion 130 to a diameter that is about the same size as that of section 73 of interior passageway 70 of valve 24. As such, when valve 24 and the luer fitting adapter 26 are assembled together, the interior passageways 136 and 70 align with each other, and the flow of fluid through the interior passageways 136 and 70 is not impeded or restricted.

The distal end 132 of the luer fitting adapter 26 has an exterior surface 150 that is substantially smooth. The distal end 132 has a notched portion 152, a band 154, a ring 156, and an O-ring receiving end 158. The notched portion 152 is sized to fit within the opening (adjacent ledge 74) to first section 71 of interior passageway 70. The band 154 has a larger diameter than notched portion 152 and is sized to snugly fit in first section 71 of the interior passageway 70 of valve 24, between the first ledge 74 and the second ledge 76. Band 154 has a smooth exterior surface to enable it and luer fitting adapter 26 to rotate in section 71 of passageway 70 of valve 24. Ring 156 has a slightly smaller diameter than band 154 and also has a smooth exterior surface (e.g. FIG. 7). Ring 156 is sized to fit between second ledge 76 and third ledge or end stop 78 of section 71 of interior passageway 70. The O-ring receiving end 158 has a slightly smaller diameter than ring 156. An O-ring 160 is positioned on the O-ring receiving end 158 wherein the O-ring 160 and O-ring receiving end 158 are sized to engage the third ledge or end stop 78 to seal the interface between the luer fitting adapter 26 and the valve 24.

One technique of assembling the main body 22, valve 24 with plug 94 attached thereto, and luer fitting adapter 26 to form hub 20 is described next. First, the valve 24 is assembled with the main body 22 by inserting the cone portion 122 of plug 94 through the proximal end 30 of the main body 22 until the plurality of threads 102 on threaded portion 86 engages the plurality of threads 46 on middle portion 34 of main body 22. At this juncture, one or both of valve 24 and main body 22 is rotated such that threads 102 and 46 engage one another and the valve 24 is forced further within main body 22. Ridge 84 on the valve 24 is positioned in the first section 39 of main body 22 such that stop ledge 40 keeps ridge 84 within the main body 22. O-ring 100 on valve 24 engages the wall of third section 43 of the interior passageway 38 of the main body 22 to seal the connection between the main body 22 and the valve 24.

Next, luer fitting adapter 26 is inserted into valve 24. O-ring receiving end 158 is inserted into first section 71 of interior passageway 70 in valve 24 until the O-ring 160 engages the third ledge or end stop 78. In this position, as mentioned previously, the first ledge 74 and the second ledge 76 are sized to retain the band 154 on the luer fitting adapter 26 and maintain the connection between the luer fitting adapter 26 and the valve 24. The third ledge or end stop 78 is sized and configured to engage the O-ring 160 placed on the O-ring receiving end 158 of the luer fitting adapter 26 to seal the connection between the luer fitting adapter 26 and valve 24.

In other embodiments, the main body 22, valve 24 with plug 94 attached thereto, and luer fitting adapter 26 are assembled in a different order to form hub 20. For example, first the luer fitting adapter 26 may be assembled with the valve 24, and then the main body 22 is assembled with the luer fitting adapter 26. Regardless of which order the main body 22, valve 24 (with plug 94), and luer fitting adapter 26 are assembled, the luer fitting adapter 26 is able to rotate independently of the valve 24. The independent rotation of the luer fitting adapter 26 allows the valve 24 to be adjusted relative to the main body 22 without loosening the connection between the luer fitting adapter 26 and the valve 24. Moreover, the luer fitting adapter 26 can be adjusted relative to the valve 24 without loosening or changing the connection between the valve 24 and the main body 22.

To stop the flow of fluid through the flow-controlling catheter hub 20, the valve 24 is moved to the closed position as illustrated in FIG. 7. To move the valve 24 to the closed position, the valve 24 is rotated clockwise (as viewed from adapter 26) such that the valve 24 moves in a distal direction towards main body 22. As the valve 24 is rotated clockwise, the engagement of threads 102 on valve 24 with threads 46 on middle portion 34 of main body 22 move valve 24 and plug 94 distally. As such, the cone portion 122 of plug 94 moves through tapered section 52 to seal part of section 52, e.g. at or adjacent to one or both of openings 57 and 58, such that fluid cannot flow past plug 94. Beneficially, as the valve 24 is rotated, the connection between the luer fitting adapter 26 and the valve 24 is not loosened or changed.

To open the flow of fluid through hub 20, the valve 24 is rotated counterclockwise (as viewed from adapter 26) such that the valve 24 moves in a proximal direction towards luer fitting adapter 26. As the valve 24 is rotated counterclockwise, the engagement of threads 102 on valve 24 and threads 46 on middle portion 34 of main body 22 move valve 24 and plug 94 proximally. As such, cone portion 122 of plug 94 moves away from tapered section 52 and openings 57 and/or 58 such that fluid flows past plug 94. If valve 24 is in the closed position, such counterclockwise rotation disengages cone portion 122 from at least part of section 52 and/or one or both of openings 57 and 58. To move the valve 24 to the fully opened position, the valve 24 is rotated counterclockwise until it reaches the fully-opened position (FIG. 9), e.g. one in which stop ledge 40 engages ridge 84. To limit the flow of fluid between the fully-opened position and the closed position, the valve 24 is rotated to a position somewhere between the closed position illustrated in FIG. 7 and the fully-opened position illustrated in FIG. 9. Thus, adjustments to flow can be easily made from any relative position of valve 24 and body 22 by rotating valve 24 either clockwise (in the illustrated embodiment) to reduce or stop flow or counterclockwise to increase flow.

The main body 22, valve 24, luer fitting adapter 26, and plug 94 are typically made of plastic or polymer material. Some examples of polymer materials include polypropylene or polycarbonate, but other types of polymer materials can be used. As can be appreciated, the main body 22 and valve 24 made of plastic enables the proximal end 30 of body 22 to flex or expand (or ridge 84 and/or other part of valve 24 to flex or compress) such that ridge 84 on the valve 24 can squeeze past the stop ledge 40 on the main body 22 when the valve 24 and main body 22 are assembled. Likewise, the luer fitting adapter 26 made of plastic enables the luer end 66 and/or band 154 to flex such that band 154 can squeeze past the first ledge 74 and fit snugly in the first section 71 of the interior passageway 70 of valve 24 between the first ledge 74 and the second ledge 76.

In another embodiment, valve 24 is made of two separate parts that are mechanically fastened together at a location between first ledge 74 and second ledge 76 after receiving the band 154 of the luer fitting adapter 26 therebetween. In this embodiment, the first part of valve 24 includes a portion of the luer end 66 that includes first ledge 74. The second part of valve 24 includes catheter end 68 and a portion of luer end 66 that includes second ledge 76. The first part is not attached to the second part until after the luer fitting adapter 26 is assembled with the second part. Beneficially, before the luer fitting adapter 26 is assembled with the valve 24, the second ledge 76 is exposed. To assemble the luer fitting adapter 26 with the second part of valve 24, the band 154 is positioned in interior passageway 70 and against the second ledge 76. Luer end 66 and/or band 154 are not required to flex to assemble the luer fitting adapter 26 with the valve 24 in this embodiment. After positioning the band 154 in the interior passageway 70 and against second ledge 76, the first part of the valve 24 is mechanically fastened to the second part of the valve 24 such that the first ledge 74 also contacts the band 154. Some techniques used to attach the first part to the second part include adhesive or ultrasonic welding. In one form, main body 22, valve 24, luer fitting adapter 26, and plug 94 are manufactured by an injection molding technique. In other embodiments, main body 22, valve 24, luer fitting adapter 26, and plug 94 are made of other materials and manufactured by other techniques.

A second embodiment of a flow-controlling catheter hub 220 is illustrated in FIGS. 10-15. Hub 220 is similar in many respects to the flow-controlling catheter hub 20, and includes a main body 222, a valve 224, a first luer fitting adapter or female luer fitting 226, and a second female luer fitting 228 configured to retain a catheter 260. The valve 224 is identical to the valve 24 described above, and so for the sake of brevity similar features will not be discussed again. Similarly, the first luer fitting adapter or female luer fitting 226 is identical to the luer fitting adapter or female luer fitting 26 described above, and similar features will not be discussed again. As described above with respect to valve 24, valve 224 is configured to limit or adjust a range of fluid flow through the main body 222 from fully opened to closed, and the luer fitting adapter 226 can be adjusted or rotated relative to the valve 224 without loosening the connection between the valve 224 and the main body 222.

Figure 10:
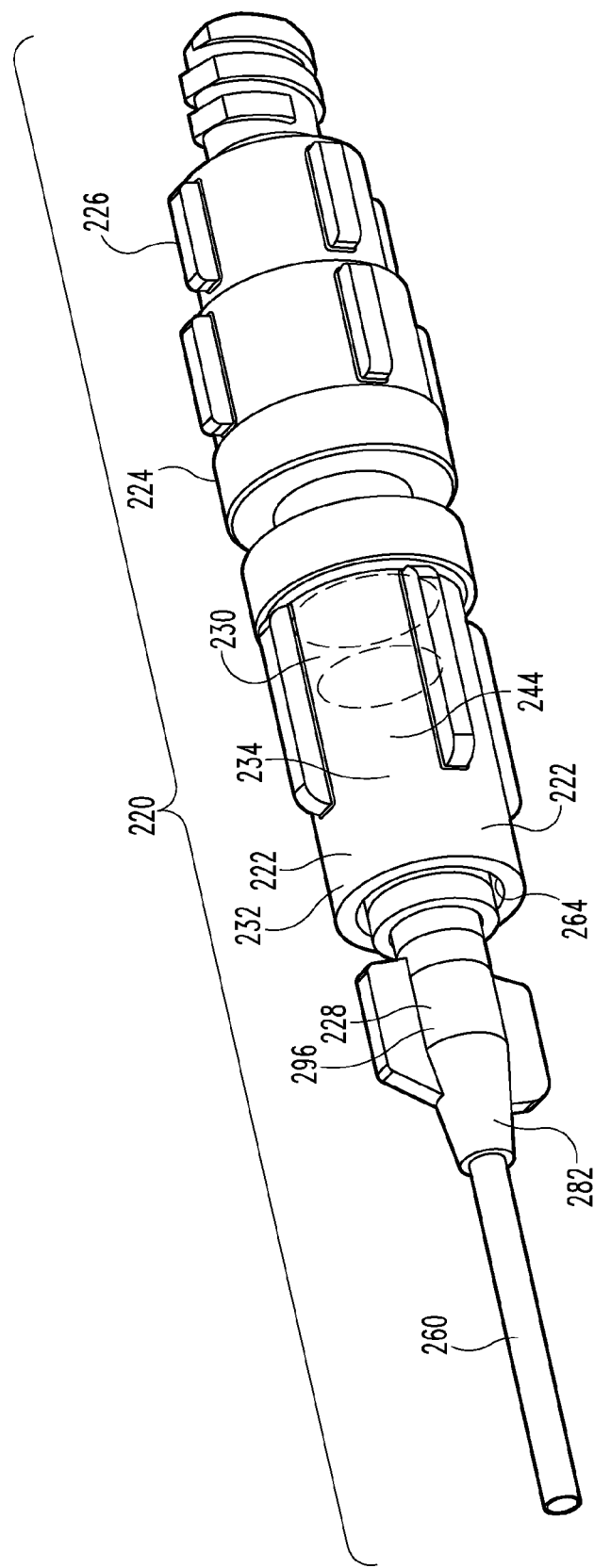
FIG. 10 is a perspective view of another embodiment of a flow-controlling catheter hub.
Figure 11:
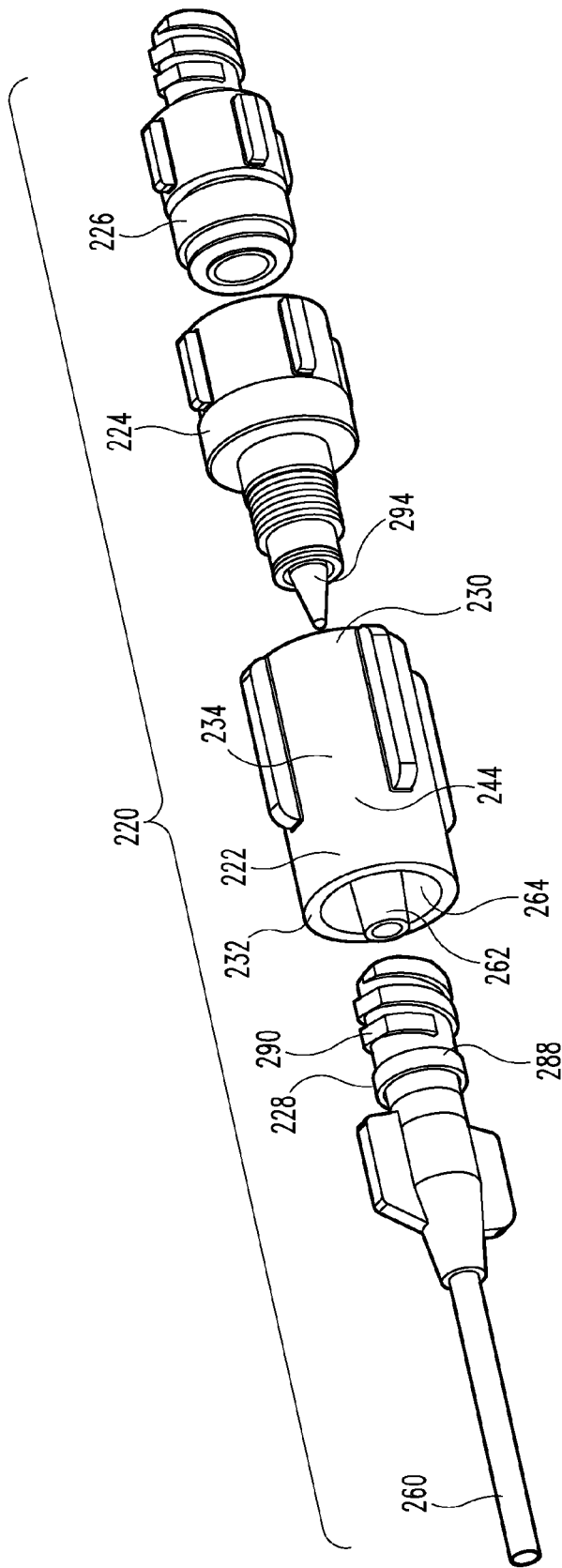
FIG. 11 is an exploded perspective view of the embodiment illustrated in FIG. 10.
Figure 12:
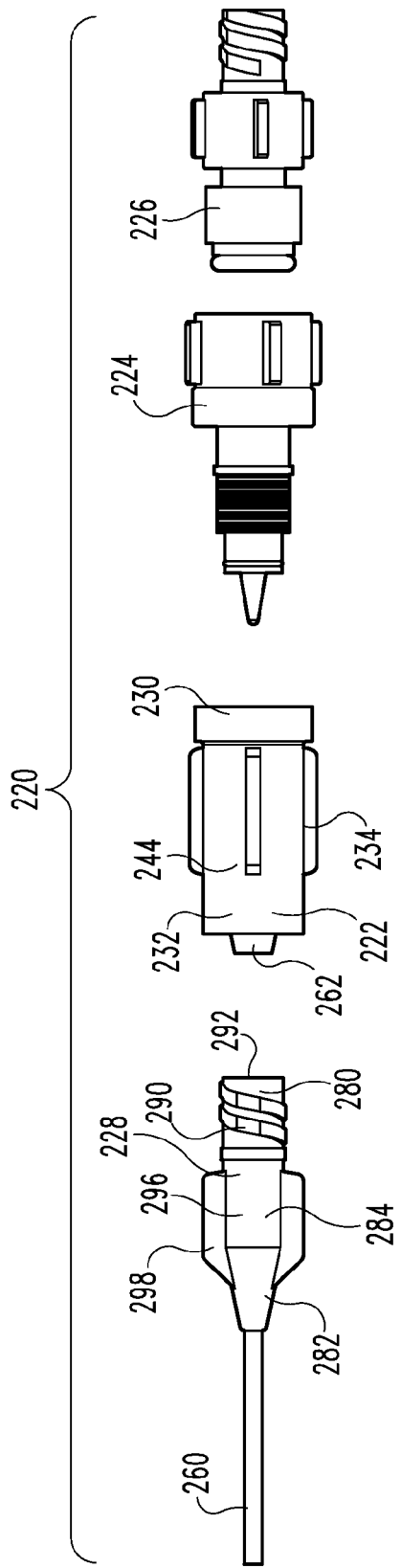
FIG. 12 is a side view of the embodiment illustrated in FIG. 11.
Figure 13:
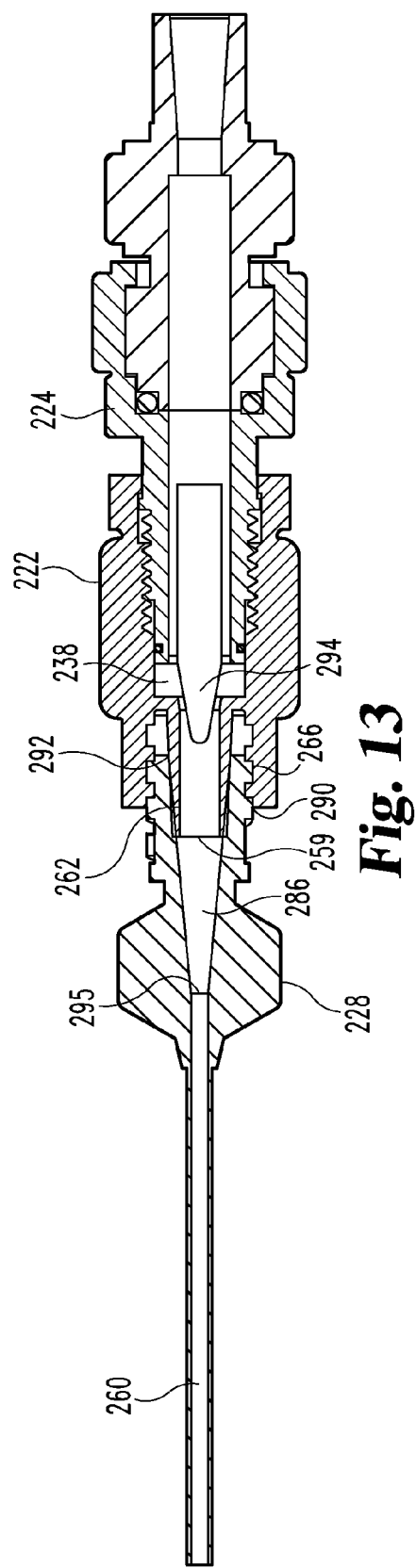
FIG. 13 is a cross-sectional view of the embodiment illustrated in FIG. 10.
Figure 14:
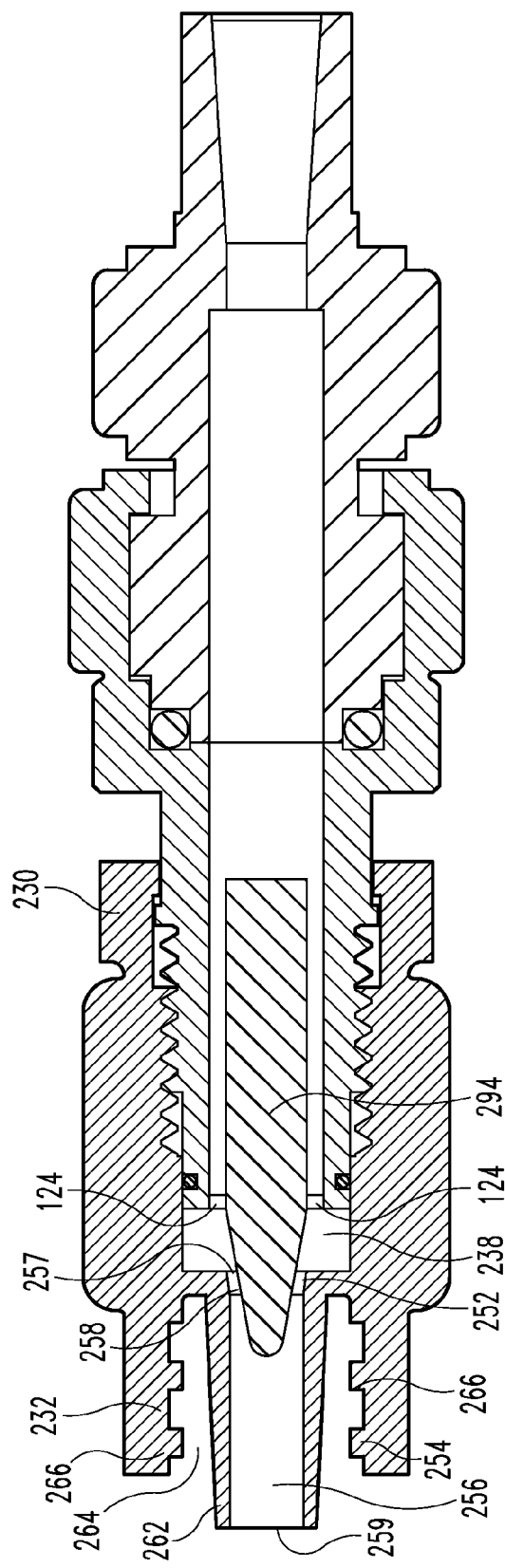
FIG. 14 is a view of the embodiment illustrated in FIG. 13 with a female luer fitting and a catheter removed.
Figure 15:
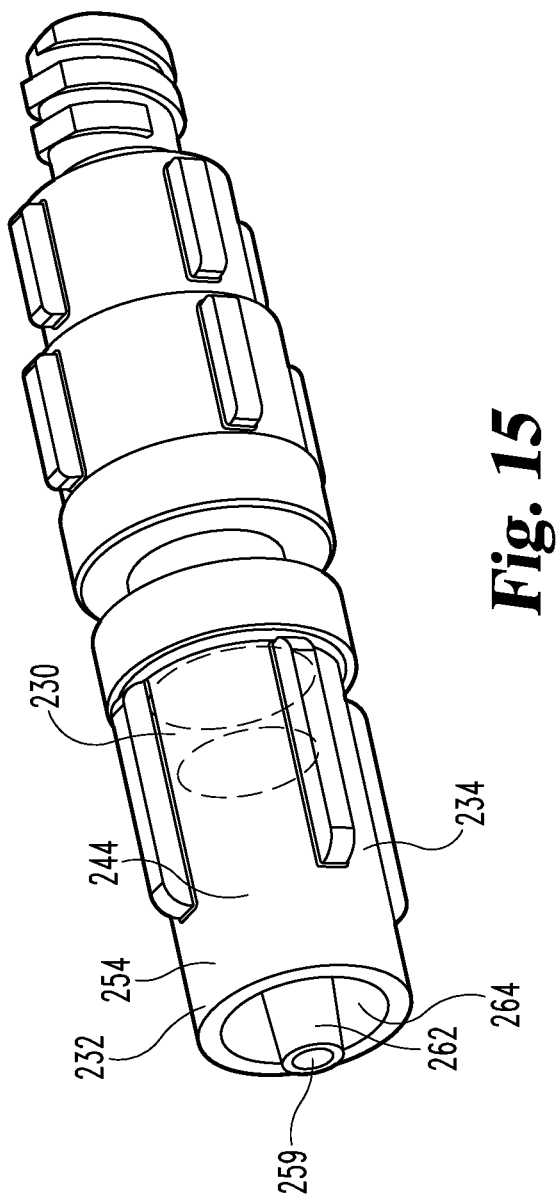
FIG. 15 is a view of the embodiment illustrated in FIG. 10 with a female luer fitting and a catheter removed.

Similar to main body 22, the main body 222 has a proximal end 230 opposite a distal end 232 and a middle portion 234 therebetween. The main body 222 includes an interior passageway 238 that is sized to receive a distal end of the valve 224. The proximal end 230 and the middle portion 234 are similar to the proximal end 30 and the middle portion 34, respectively, of the main body 22, therefore similar features will not be discussed. As illustrated in FIGS. 10 and 15, the middle portion 234 includes an exterior surface 244 that extends to the distal end 232. Exterior surface 244 does not taper in this embodiment. Additionally, the distal end 232 defines a recess 264 defined circumferentially around an extension 262 as described in more detail below. The recess 264 includes threads 266 sized to mate with threads 290 on second female luer fitting 228, as illustrated in FIGS. 13 and 14. Interior passageway 238 is similar to interior passageway 38, but interior passageway 238 extends through extension 262.

The distal end 232 is configured differently than distal end 32 described above. Distal end 232 has a fourth section 252 and a fifth section 256 of the interior passageway 238, and an extension 262 as illustrated in FIGS. 14 and 15. Fourth section 252 of the interior passageway 238 is tapered from a first opening 257 that is sized to receive a cone portion of a plug 294 attached to valve 224 to a smaller second opening 258. The taper of the fourth section 252 is about the same slope as the cone portion of the plug 294 attached to valve 224. In other embodiments, fourth section 252 is configured differently. The extension 262 defines the fifth section 256 of the interior passageway 238 which starts at second opening 258 and spans to a distal opening 259. Distal opening 259 is smaller than a first opening 292 in an interior passageway 286 of second female luer fitting 228. Extension 262 extends beyond the distal end 232. In the illustrated embodiment, extension 262 is a conic shape that includes tapered walls, while in other embodiments extension 262 has substantially straight walls. Second female luer fitting 228 includes a proximal end 280 opposite a distal end 282, a middle portion 284 between the proximal end 280 and the distal end 282, and an interior passageway 286 that spans from the proximal end 280 to the distal end 282. The proximal end 280 includes an exterior surface 288 with a plurality of threads 290 that are configured to mate with the plurality of threads 266 in the recess 264 to connect the second female luer fitting 228 to the main body 222.

As illustrated in FIG. 13, the interior passageway 286 of fitting 228 is tapered from a first opening 292 that is sized to receive extension 262 to a second opening 295 that is sized to receive the catheter 260. Second opening 295 is about the same or slightly smaller than the diameter of catheter 260 to thereby retain catheter 260 by a friction fit or an interference fit. The middle portion 284 has an exterior surface 296 and a plurality of ridges 298 that aid a user in gripping the second female luer fitting 228. The distal end 282 is tapered from the middle portion 284 to about the diameter of the catheter 260.

The first luer fitting adapter or female luer fitting 226 is connected to the valve 224 as described above with respect to luer fitting adapter 26 and valve 24. Likewise, the valve 224 is connected to the main body 222 as described above with respect to valve 24 and main body 22. Additionally, the plug 294 on the valve 224 is inserted into fourth section 252 and fifth section 256 of the interior passageway 238 of the main body 222. The main body 222 is connected to the second female luer fitting 228 by inserting the extension 262 into the first opening 292 and the interior passageway 286. The plurality of threads 290 on the exterior surface 288 are threaded with the plurality of threads 266 in the recess 264 to attach the main body 222 with the second female luer fitting 228.

In a closed position, the plug 294 engages a portion of the interior of extension 262, e.g. at or adjacent first opening 257 and/or second opening 258, to block fluid flow through the fifth section 256 of the interior passageway 238 of the main body 222 and the interior passageway 286 of second female luer fitting 228. In an open position, the plug 294 does not contact first opening 257 or second opening 258; therefore, fluid can flow through the fifth section 256 of the interior passageway 238 of the main body 222 and the interior passageway 286 of second female luer fitting 228.

If vasculature access is desired after the catheter 260 is positioned within a patient, hub 220 can be detached from catheter 260 by uncoupling the main body 222 from the second female luer fitting 228. In the illustrated embodiment to detach main body 222 from second female luer fitting 228, main body 222 is rotated about second female luer fitting 228 to unthread the threads 290 from threads 266. Then the main body 222, valve 224, and first luer fitting adapter or female luer fitting 226 are removed from second female luer fitting 228. The second female luer fitting 228 remains connected to the catheter 260, and the medical practitioner is able to insert a medical device through interior passageway 286 and into the catheter 260 to gain access to the patient's vasculature. The main body 222, valve 224, and first luer fitting adapter or female luer fitting 226 do not need to be disassembled to gain access to the patient's vasculature. Beneficially, another incision may not be necessary since the catheter 260 is already inserted into the patient's vasculature and the flow-controlling catheter hub 220 can be disassembled without disturbing the catheter.

After the medical procedure is complete, the main body 222, valve 224, and first luer fitting adapter or female luer fitting 226 can be reattached to catheter 260 by coupling the main body 222 to the second female luer fitting 228 as described above.

While the disclosure has been illustrated and described in detail in the drawings and foregoing description, the same is to be considered as illustrative and not restrictive in character, it being understood that only the preferred embodiment has been shown and described and that all changes, equivalents, and modifications that come within the spirit of the disclosures defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An apparatus to adjust fluid flow to a catheter, the apparatus comprising:
a plug having a cylindrical shaft portion and a cone portion;
a valve having a luer end opposite a catheter end and defining an interior passageway between the luer end and the catheter end, the catheter end being configured to connect with a proximal end of a main body, the catheter end being also configured to receive the cylindrical shaft portion of the plug wherein the plug is fixedly attached to the interior passageway of the valve thereby preventing movement of the plug relative to the valve, wherein the cone portion of the plug extends from the catheter end, and wherein the luer end is configured to receive a distal end of a luer fitting adapter;
the main body having a distal end opposite a proximal end and defining an interior passageway between the distal end and the proximal end, the proximal end being configured to receive the catheter end of the valve, the distal end being configured to receive a portion of the catheter, the interior passageway includes a portion that is tapered to selectively receive the cone portion of the plug so that the amount of fluid flow through the distal end is adjustable between a closed position and a fully opened position; and
the luer fitting adapter having a distal end opposite a proximal end and defining an interior passageway between the distal end and the proximal end, wherein the distal end is configured to connect with the luer end of the valve, wherein the luer fitting adapter is configured to move independently of the valve and the main body.

2. The apparatus of claim 1, wherein both of the catheter end of the valve and the proximal end of the main body include threads to threadably engage each other to couple the valve with the main body.

3. The apparatus of claim 1, wherein the taper of the interior passageway of the main body is approximately the same as a taper on the cone portion of the plug.

4. The apparatus of claim 1, wherein the valve includes a ridge on an exterior surface, and the interior passageway of the main body includes a stop ledge near the proximal end to contact the ridge and retain the catheter end of the valve within the main body.

5. The apparatus of claim 1, wherein the distal end of the luer fitting adapter has a band portion with a substantially smooth exterior surface, and the interior passageway of the valve includes a first ledge and a second ledge to retain the band portion therebetween.

6. The apparatus of claim 5, further comprising:
an O ring positioned on the distal end of the luer fitting adapter; and
wherein the interior passageway of the valve includes a third ledge wherein the O ring and the third ledge are configured to form a seal between the luer fitting adapter and the valve.

7. The apparatus of claim 1, further comprising:
at least one leg that extends between the plug and the interior passageway of the valve to attach the plug to the interior passageway the valve.

8. An apparatus to adjust fluid flow to a catheter, the apparatus comprising:
a plug having a cylindrical shaft portion and a cone portion;
a main body defining an interior passageway, the interior passageway includes a tapered portion to selectively receive the cone portion of the plug wherein the tapered portion has a surface that is parallel to the cone portion, the main body configured to connect with the catheter;
a valve defining an interior passageway sized to receive the plug, the plug is fixedly attached to the interior passageway of the valve thereby preventing movement of the plug relative to the valve, the valve being assembled with the main body wherein the interior passageways are aligned and the cone portion of the plug is configured to enter the tapered portion and the interior passageway of the main body, the valve being configured to selectively move in the main body between a closed position wherein no fluid flows through the interior passageway of the main body and a fully opened position wherein a maximum amount of fluid flows through the interior passageway of the main body; and
a luer fitting adapter defining an interior passageway, the luer fitting adapter is assembled with the valve wherein the interior passageways are aligned, and the luer fitting adapter is configured to move independently of the main body and the valve.

9. The apparatus of claim 8, wherein the valve and the main body each include threads to threadably engage each other to couple the valve with the main body.

10. The apparatus of claim 8, wherein the valve includes a ridge on an exterior surface, and the interior passageway of the main body includes a stop ledge to contact the ridge and retain the valve assembled with the main body.

11. The apparatus of claim 8, wherein the cone portion of the plug extends from the valve to engage the interior passageway of the main body when the valve is in the closed position.

12. The apparatus of claim 8, further comprising:
the main body defines a cone-shaped recess and an extension positioned in the recess, the interior passageway of the main body extends through the extension; and
a second luer fitting adapter defining an interior passageway sized to receive the extension of the main body to enable fluid flow through the interior passageways of the main body and the second luer fitting adapter, the second luer fitting adapter is selectively connected to the main body.

13. The apparatus of claim 12, wherein the second luer fitting adapter and the main body each include threads to threadably engage each other to couple the main body with the second luer fitting adapter.

14. The apparatus of claim 8, further comprising:
a plurality of legs that extend around an exterior surface of the plug, the plurality of legs are configured to attach the plug to the interior passageway of the valve.

15. An apparatus to adjust fluid flow to a catheter, the apparatus comprising:
a plug having a cylindrical shaft portion and a cone portion;
a valve defining an interior passageway, the plug is fixedly attached to the interior passageway of the valve thereby preventing movement of the plug relative to the valve;
a first luer fitting adapter defining an interior passageway, the first luer fitting adapter being rotatably assembled with the valve wherein the interior passageways are aligned, and the first luer fitting adapter is configured to move independently of a main body and the valve;
the main body having a distal end opposite a proximal end and defining an interior passageway between the distal end and the proximal end, the interior passageway includes a tapered portion to selectively receive the cone portion of the plug to adjust fluid flow, the main body being assembled with the valve wherein the interior passageways are aligned and the valve being configured to move between a closed position wherein no fluid flows through the interior passageway of the main body and an open position wherein fluid flows through the interior passageway of the main body, the main body also including a stop ledge configured to engage and retain the valve in the main body when the valve is in the open position; and
a second luer fitting adapter defining an interior passageway, the second luer fitting adapter being connected with a portion of the catheter and the second luer fitting adapter is detachably assembled with the main body wherein the interior passageways are aligned.

16. The apparatus of claim 15, wherein the first luer fitting adapter includes a band portion having a substantially smooth exterior surface and the interior passageway of the valve includes a first ledge and a second ledge positioned to retain the band portion therebetween.

17. The apparatus of claim 15, wherein both the valve and the main body include threads to threadably engage each other to couple the valve with the main body.

18. The apparatus of claim 15, further comprising:
the cone portion extends from the valve to engage the interior passageway of the main body when the valve is in the closed position.

19. The apparatus of claim 18, wherein the main body defines a cone-shaped recess and an internal cone positioned in the recess, the interior passageway of the main body extends through the internal cone.

20. The apparatus of claim 15, wherein both the second luer fitting adapter and the main body include threads to threadably engage each other to couple the second luer fitting adapter with the main body.

* * * * *